US012558498B2

(12) United States Patent
Hersbach et al.

(10) Patent No.: US 12,558,498 B2
(45) Date of Patent: *Feb. 24, 2026

---

(54) ELECTRONIC INHALER AND METHOD FOR ADJUSTING THE SAME

(71) Applicant: GILBERT TECHNOLOGIES BV, Eindhoven (NL)

(72) Inventors: Georgius Josephus Maria Hersbach, Loosdrecht (NL); Gabriel Marinus Henricus Meesters, Delft (NL); Sheila Khodadadi, Rijswijk (NL)

(73) Assignee: GILBERT TECHNOLOGIES BV, Eindhoven (NL)

( * ) Notice: Subject to any disclaimer, the term of this patent is extended or adjusted under 35 U.S.C. 154(b) by 749 days.

This patent is subject to a terminal disclaimer.

(21) Appl. No.: 17/919,123

(22) PCT Filed: Apr. 15, 2021

(86) PCT No.: PCT/NL2021/050243
§ 371 (c)(1),
(2) Date: Oct. 14, 2022

(87) PCT Pub. No.: WO2021/210980
PCT Pub. Date: Oct. 21, 2021

(65) Prior Publication Data
US 2023/0158258 A1 May 25, 2023

(30) Foreign Application Priority Data
Apr. 17, 2020 (NL) ...................................... 2025368

(51) Int. Cl.
*A61M 11/00* (2006.01)
*A24F 40/05* (2020.01)
(Continued)

(52) U.S. Cl.
CPC ............. *A61M 15/02* (2013.01); *A24F 40/05* (2020.01); *A61M 15/0021* (2014.02); *A61M 15/06* (2013.01); *A61M 11/001* (2014.02)

(58) Field of Classification Search
None
See application file for complete search history.

(56) References Cited

U.S. PATENT DOCUMENTS

| | | | | |
|---|---|---|---|---|
| 5,813,614 A | * | 9/1998 | Coffee | B05B 5/0255 |
| | | | | 239/690 |
| 6,684,879 B1 | * | 2/2004 | Coffee | A61M 15/008 |
| | | | | 128/200.14 |

(Continued)

FOREIGN PATENT DOCUMENTS

KR 20190123977 A * 11/2019 ........... A24F 47/002

OTHER PUBLICATIONS

KR10290123977 Translation (Year: 2019).*
International Search Report for PCT/NL2021/050243, Prepared by the European Patent Office, Mailing date Jun. 14, 2021, 3 pages.

*Primary Examiner* — Timothy A Stanis
(74) *Attorney, Agent, or Firm* — Brooks Kushman P.C.

(57) ABSTRACT

An inhaler and a method for adjusting the inhaler for inhaling a liquid pharmaceutical formulation and an inhaler with a nozzle for use with said method. The inhaler includes a mouth piece portion with a lumen and a coupled body portion. The body portion includes a body with a base facing the lumen. The body further has a nozzle with an outlet for discharging said pharmaceutical formulation extending from the base into the lumen, a counter electrode at the base at a counter electrode distance from the nozzle outlet and a discharge electrode at a discharge electrode distance from the nozzle outlet. The inhaler further has a power supply and (Continued)

Figure 1A:
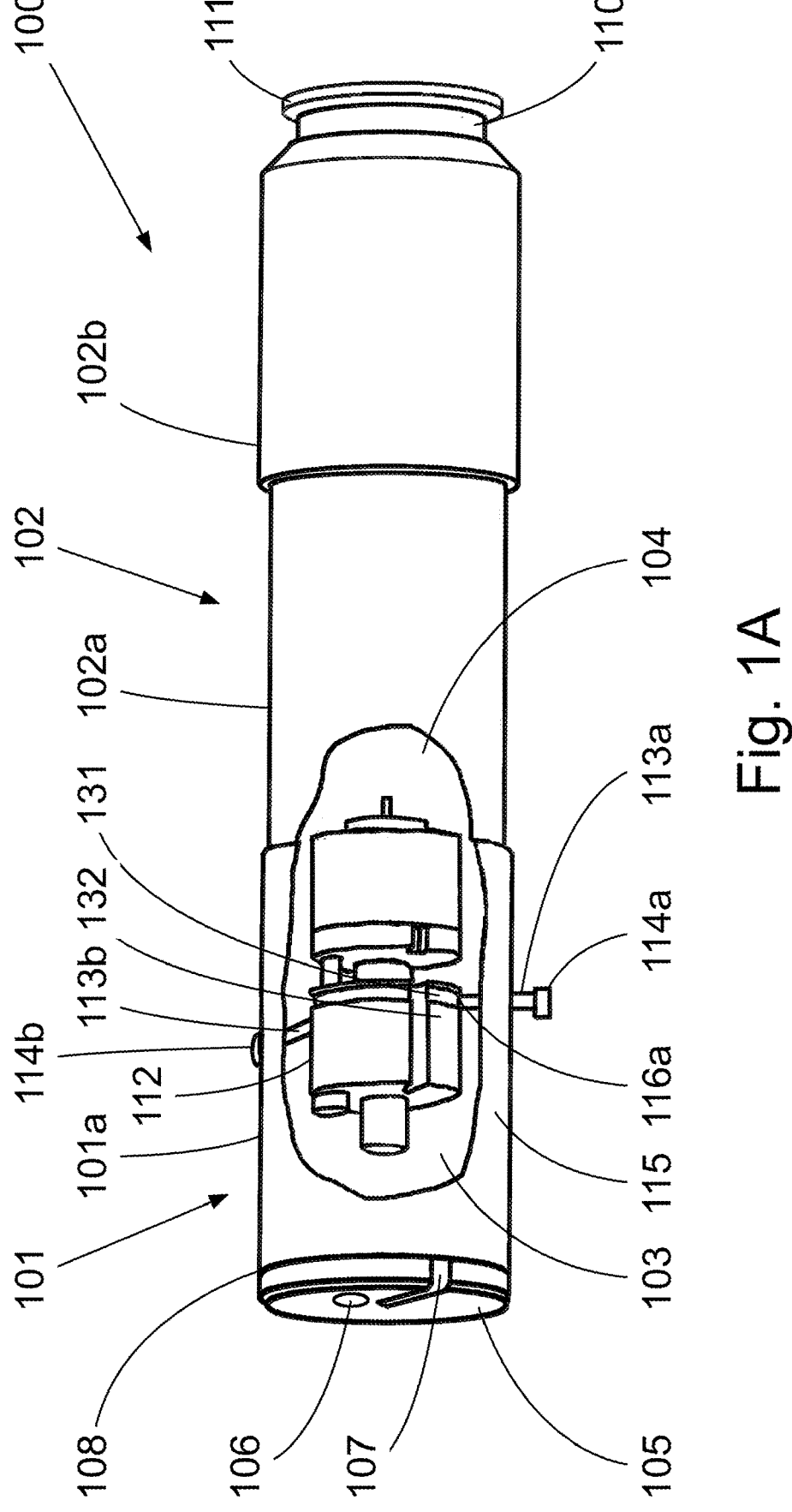

an air inlet. The method includes a step of adjusting the electrode(s) relative to the nozzle outlet of the inhaler.

21 Claims, 3 Drawing Sheets

(51) Int. Cl.
    *A61M 15/00*        (2006.01)
    *A61M 15/02*        (2006.01)
    *A61M 15/06*        (2006.01)

(56) References Cited

U.S. PATENT DOCUMENTS

| | | | |
|---|---|---|---|
| 2010/0083956 A1 | 4/2010 | Fukumoto et al. | |
| 2015/0251201 A1* | 9/2015 | Hradetzky | A61M 15/02 |
| | | | 239/690 |
| 2017/0136194 A1 | 5/2017 | Cameron | |
| 2019/0209791 A1 | 7/2019 | Courbat et al. | |
| 2019/0230982 A1* | 8/2019 | Inagaki | A24B 15/32 |
| 2022/0273031 A1* | 9/2022 | Bialek | A24F 40/48 |

* cited by examiner

ELECTRONIC INHALER AND METHOD FOR ADJUSTING THE SAME

CROSS-REFERENCE TO RELATED APPLICATION

This application is the U.S. national phase of PCT Application No. PCT/NL2021/050243 filed on Apr. 15, 2021, which claims priority to NL Patent Application No. 2025368 filed on Apr. 17, 2020, the disclosures of which are incorporated in their entirety by reference herein.

The present invention relates to a method for adjusting an inhaler for inhaling a liquid pharmaceutical formulation, the method for adjusting the inhaler using an inhaler, said inhaler comprising:

a mouth piece portion comprising a circumferential wall extending from the edges of an inhalation opening, said circumferential wall enveloping a lumen, and a body portion coupled to the mouth piece portion, the body portion comprising a body with a base, said base facing the lumen and defining a limit of the lumen of the mouth piece portion, said body further comprising:

i) a nozzle comprising a nozzle inlet at a first end of the nozzle for receiving a liquid pharmaceutical formulation and a nozzle outlet at a second end of the nozzle for discharging said pharmaceutical formulation, wherein the nozzle passes through the base and a portion of the nozzle comprising the nozzle outlet extends into the lumen, ii) a counter electrode arranged at the base relatively close to the nozzle at a counter electrode distance from the nozzle outlet, said counter electrode distance defining an electric field path, iii) a discharge electrode comprising a discharge portion arranged relatively far from the nozzle as compared to the counter electrode, said discharge portion being at a discharge electrode distance from the nozzle outlet, wherein the discharge electrode distance is larger than the counter electrode distance;

the inhaler further comprising:

a power supply electrically connected to at least one of the nozzle, the counter electrode and the discharge electrode, and an air inlet for allowing air for inhaling to enter the lumen.

Electronic inhalers are able to atomize liquid pharmaceutical formulations and are well known in the art, this includes the production and the tuning of said inhalers. Their advantages compared to manual inhalers are manifold, amongst others a relatively homogeneous particle size through atomization, and as a consequence better delivery, and more accurate dosing compared to mechanical or pressurized inhalers.

These electronic inhalers comprise a body portion with an air inlet through which an air stream may pass. The air inlet is fluidly connected to a lumen within a mouth piece portion comprising an inhaling opening arranged adjacent to the body portion. Within said lumen a liquid pharmaceutical formulation may be atomized and the atomized pharmaceutical formulation carried by the air stream may be inhaled by a user through the inhaling opening. A nozzle outlet at the end of a nozzle debouches into the lumen of the mouth piece portion and is arranged for atomization of the liquid pharmaceutical composition into the lumen. Typically the nozzle is a thin capillary needle having at one end a nozzle inlet allowing a liquid pharmaceutical formulation contained within a reservoir to enter the nozzle. The reservoir may be provided with the inhaler fluidly connected to the nozzle inlet, but a reservoir may also be provided later for example as a replacement charge. A pump may be provided but is not essential to its functioning, capillary force generated by the nozzle or a pressurized reservoir may provide for a suitable flow of the liquid pharmaceutical formulation through the nozzle as well. A pump may be preferred. The nozzle also has a nozzle outlet through which the pharmaceutical formulation is passed and from which the pharmaceutical formulation is atomized into the lumen of the mouth piece portion. Typically the user causes the air stream through the lumen by inhalation, said air stream carrying the atomized pharmaceutical formulation to the target tissue of respiratory system of a user.

In order to atomize the liquid pharmaceutical formulation into the lumen a Taylor cone is established at the nozzle outlet by means of a potential between the nozzle and a counter electrode. This is typically a stable Taylor cone with a single jet, but may be a temporary Taylor cone as well. A Taylor cone is a typical cone shaped volume of liquid. The Taylor cone presents a tip from which a jet emerges. At a distance from the Taylor cone the jet breaks up in charged liquid particles, in the order of 0.1 to 10 micrometers for the purpose of inhaling pharmaceutical formulations, that move away from the Taylor cone. The electric field strength between the counter electrode and the nozzle outlet is amongst others a major determinant of the particle size that atomize from the jet. These atomized particles together make up a spray in the air within the lumen of the mouth portion and the spray may be inhaled with an air stream caused by inhalation of a user. It is important that the spray is largely discharged and comprises a relatively homogeneous distribution of particle size in order to be delivered efficiently to a selected respiratory system tissue. The discharge of the particles in the spray is achieved by a discharge electrode having a sharp tips serving as discharge portion, from which discharge portion corona particles having an opposite charge with respect to the spray particles may be emitted. These corona particles collide and fuse with the particles in the spray and thus cause discharge of the spray.

A drawback of prior art electronic inhalers is that they are designed and manufactured accordingly for delivering a specific pharmaceutical formulation to a specific tissue of the respiratory system, each formulation requiring manufacture of a different inhaler with different specifications.

The object of this invention is to provide for a method for adjusting electronic inhalers after being manufactured for delivery of a selected pharmaceutical formulation to a selected tissue of the respiratory system.

To this end, a method according to the preamble is characterized in that the method comprises a step of adjusting the discharge electrode distance.

In this way inhalers may be manufactured cheaply producing a single model and after manufacture inhalers may be adjusted to the specifications required for use with a selected liquid pharmaceutical formulation. Thus a single production line is required making a identical batches of inhalers without the need for stopping production and changing components. This may also provide for a reduction in error in the manufacturing process in which wrong components may be incorporated into inhalers. The skilled person is able to determine which counter electrode distance is required for atomization of a selected liquid pharmaceutical formulation into a spray with a desired particle size and spray shape for delivery to a selected tissue of the respiratory system.

Setting the nozzle outlet at appropriate distance from the discharge electrode may produce a spray that is wide enough to ensure particle size remains homogeneous but the spray is also narrow enough to reduce loss of the atomized pharmaceutical formulation on the circumferential wall of the mouth portion of the inhaler improving the delivery of liquid pharmaceutical formulation by the inhaler to any selected target tissue of the respiratory system.

The method may also comprise a step of adjusting the counter electrode distance.

Setting the nozzle outlet relatively close to the counter electrode may produce a spray for improved delivery to the alveolear tissue. Setting the nozzle outlet at increasing distance from the counter electrode may produce a spray for improved delivery to any tissue chosen from the alveoli, bronchioles, bronchi or trachea respectively.

The setting of the nozzle outlet at an appropriate distance from the counter electrode and/or the discharge electrode for targeting delivery of the atomized pharmaceutical formulation a specific tissue of the respiratory system is not universal for different pharmaceutical formulations, even changes in concentrations affect the atomization. It is necessary to determine appropriate settings for each different liquid pharmaceutical formulation, which determination can be performed by any skilled person by determining the particle size in the spray. These settings comprise the potential to be established on the nozzle, counter electrode and discharge electrode, wherein the counter electrode is often set at 0 Volt, and further comprise according this invention the counter electrode distance and/or discharge electrode distance, which may be set after production for fine tuning the inhaler for use with a desired liquid pharmaceutical formulation.

US2019209791 describes an inhaler of which the discharge electrode distance can be chosen while manufacturing the inhaler in order to avoid electrical breakdown of the air, but does not disclose an inhaler of which the discharge electrode distance may be adjusted after manufacturing in order to control a width of the spray.

According to a favourable embodiment, the inhaler further comprises an discharge electrode actuator capable of moving the nozzle and the discharge electrode with respect to each other; and wherein in the method the step of adjusting the discharge electrode distance is performed by moving the nozzle and discharge electrode with respect to each other.

In this way a more precise adjustment is possible. The inhaler may be adjusted and may be readjusted if it is detected that the adjustment is not according the appropriate settings for delivery of a selected liquid pharmaceutical formulation to a selected tissue of the respiratory system. The discharge of the spray regulates the dimension and thereby the efficiency of delivery to the target tissue, if the spray is oversized for the mouth piece portion part will be lost on the inner surface of the circumferential wall thereof.

According to a favourable embodiment, the inhaler further comprises a discharge electrode securing means for securing the nozzle in a position relative to the discharge electrode; and the method further comprises a step of securing the nozzle in a position relative to the discharge electrode.

In this way the method provides for an inhaler with a consistent performance. The discharge electrode distance may be securely fixed, eventually after adjusting the portion of the nozzle extending into the lumen, at a desired distance providing for an inhaler that maintains the desired characteristics and is less prone to accidental readjustment or tampering. The method may thus further comprise the step of securing the nozzle in a position relative to the discharge electrode subsequent the step of adjusting or readjusting the discharge electrode distance. Preferably the discharge electrode securing means can only be operated by the person authorized for market authorization of the inhaler so its function is and remains in conformity with requirements.

According to a favourable embodiment, the step of adjusting the counter electrode distance is performed by truncating the portion of the nozzle extending into the lumen.

In this way a relatively long portion of the nozzle can be cheaply modified and the discharge electrode distance reduced without the need for adjustment means for adjusting the portion of the nozzle extending into the lumen. This allows manufacture of a very cheap inhaler that after production may be modified to desired needs. Truncating the nozzle portion removes the old nozzle outlet and creates a new nozzle outlet at the desired counter electrode distance from the counter electrode. The skilled person can determine using his common general knowledge the length to which the portion extending into the lumen should be truncated for the desired characteristics. Once determined this step can be executed to all inhalers to be used for the same liquid pharmaceutical formulation to be targeted to the same tissue.

According to a favourable embodiment, the inhaler further comprises a counter electrode actuator capable of moving the nozzle and the counter electrode with respect to each other; and wherein in the method the step of adjusting the counter electrode distance is performed by moving the nozzle and the counter electrode with respect to each other.

In this way a more precise adjustment is possible. The inhaler may be adjusted and may be readjusted if it is detected that the adjustment is not according the appropriate settings for delivery of a selected liquid pharmaceutical formulation to a selected tissue of the respiratory system.

According to a favourable embodiment, the inhaler further comprises a counter electrode securing means for securing the nozzle in a position relative to the counter electrode; and the method further comprises a step of securing the nozzle in a position relative to the counter electrode.

In this way the method provides for an inhaler with a consistent performance. The counter electrode distance may be securely fixed, eventually after adjusting the portion of the nozzle extending into the lumen, at a desired distance providing for an inhaler that maintains the desired characteristics and is less prone to accidental readjustment or tampering. The method may thus further comprise the step of securing the nozzle in a position relative to the counter electrode subsequent the step of adjusting or readjusting the counter electrode distance. Preferably the counter electrode securing means can only be operated by the person authorized for market authorization of the inhaler so its function is and remains in conformity with requirements.

According to a favourable embodiment, the nozzle of the inhaler is a removable nozzle; and wherein in the method the step of adjusting the counter electrode distance is performed by replacing the removable nozzle with a replacement nozzle, said replacement nozzle being shorter or longer with respect to the removable nozzle or being of a same size as the removable nozzle.

In this way a produced inhaler suitable for one purpose may be converted to an inhaler suited for delivery of a different liquid pharmaceutical formulation and/or for targeting a different tissue of the respiratory system by simply replacing the removable nozzle with a replacement nozzle said replacement nozzle, after insertion, comprising a portion extending into the lumen further or less far compared to the removable nozzle. Hence a producer can for example respond quickly to changes in market needs by quickly and cheaply converting inhalers. The inhaler may also be refurbished in this way with an identical replacement nozzle when the functioning after prolonged use may be altered by accumulation of dirt or components of the liquid pharmaceutical formulation at or within the nozzle or at the nozzle outlet, or by abrasion of the nozzle or a nozzle coating. The refurbishment of the inhaler with a clean and unused replacement nozzle of identical size thus allows adjusting the inhaler to the original desired setting.

According to a favourable embodiment, the nozzle, preferably at the portion of the nozzle extending into the lumen, comprises a marking; and
during the step of adjusting the counter electrode distance the marking is used for guiding said adjusting.

In this way a visual inspection allows to check proper assembly and setting of the inhaler. The nozzle allows for easy adjustment by visual inspection of the location of the marking or cutting at the marking. Visual inspection of the marking relative to base with the counter electrode arranged at it may also indicate that the nozzle is not properly engaged with the nozzle part resulting in poor or improper functioning. For example, a marking may indicate nozzle outlet distance or distance to the base. A marking may consist of an etching or an engraving on the nozzle, or applying a marking or a coating with marking on the nozzle.

The present invention also relates to an inhaler for inhaling a liquid pharmaceutical formulation, said inhaler comprising:
- a mouth piece portion comprising a circumferential wall extending from the edges of an inhalation opening, said circumferential wall enveloping a lumen, and
- a body portion coupled to the mouth piece portion, the body portion comprising a body with a base, said base facing the lumen and defining a limit of the lumen of the mouth piece portion said body further comprising:
  - i) a nozzle comprising a nozzle inlet at a first end of the nozzle for receiving a liquid pharmaceutical formulation and a nozzle outlet at a second end of the nozzle for discharging said pharmaceutical formulation, wherein the nozzle passes through the base and a portion of the nozzle comprising the nozzle outlet extends into the lumen,
  - ii) a counter electrode arranged at the base relatively close to the nozzle at a counter electrode distance from the nozzle outlet, said counter electrode distance defining an electric field path,
  - iii) a discharge electrode comprising a discharge portion arranged relatively far from the nozzle, said discharge portion at a discharge electrode distance from the nozzle outlet, wherein the discharge electrode distance is larger than the counter electrode distance;
the inhaler further comprising:
- a power supply electrically connected to at least one of the nozzle, the counter electrode and the discharge electrode, and
- an air inlet for allowing air for inhaling to enter the lumen.

The present invention also relates to an electronic inhaler according the preamble of claim 1. For the sake of brevity it is stated that these inhalers suffer from the same draw back as mentioned in the preamble discussion of claim 1.

The object of this invention is to provide for an inhaler that after manufacture is adjustable for improved delivery of a selected liquid pharmaceutical formulation to a selected tissue of the respiratory system.

To this end, an inhaler according to the preamble is characterized in that the discharge electrode distance is adjustable.

In this way a cheap inhaler is provided and is adjustable after manufacture to the specifications required for use with a selected liquid pharmaceutical formulation. The inhaler may be adjusted by an authorized or qualified person skilled in doing so. The adjustment of the inhaler according the invention can be performed just after manufacture at the manufacturing site, or can be performed later by for example an market authorized provider, general practitioner or a pharmacist to ensure proper dosing and targeting of the liquid pharmaceutical formulation to the selected tissue of the respiratory system.

According to a favourable embodiment, the discharge electrode comprises a plurality of discharge portions, preferably at least 3, more preferably at least 4, and even more preferably at least 6, said discharge portions at equal discharge electrode distance from the nozzle outlet and evenly spread around the longitudinal axis of the portion of the nozzle extending into the lumen.

In this way the discharge of the spray will be more uniform.

According to a favourable embodiment, the nozzle and the discharge electrode are movable with respect to each other along a direction of the longitudinal axis of the portion of the nozzle extending into the lumen.

In this way the discharge electrode distance may be adjusted along a single axis with less concern regarding the three dimensional arrangement of the nozzle, the counter electrode and the discharge electrode make adjustment easier.

According to a favourable embodiment, the discharge portions are located outside the lumen.

In this way interference with Taylor cone, jet and/or spray formation by the discharge electrode is reduced and may result in improved efficiency of delivery of the pharmaceutical formulation.

According to a favourable embodiment, a distal end of the discharge portion is directed to the longitudinal axis of the portion of the nozzle extending into the lumen.

In this way the discharge of a spray may be improved. Because the corona discharge particles move away from the distal end in the direction in which said distal end is pointing it is preferred to direct the distal end towards a volume of the lumen associated with nozzle outlet in which a jet and a spray is to be formed. Preferably the angle between the distal end and the base is between 25°-85°, more preferable between 30-80, and even more preferable between 35-75.

According to a favourable embodiment, the nozzle, preferably at the portion of the nozzle extending into the lumen, comprises a marking.

In this way a visual inspection allows to check proper assembly and setting of the inhaler. The nozzle allows for easy adjustment by visual inspection of the location of the marking or cutting at the marking. Visual inspection of the marking relative to base with the counter electrode arranged at it may also indicate that the nozzle is not properly engaged with the nozzle part resulting in poor or improper functioning. For example, a marking may indicate nozzle outlet distance or distance to the base. Markings may consist of an etching or an engraving on the nozzle, or an applied marking or a coating with a marking on the nozzle.

According to a favourable embodiment, the counter electrode distance is adjustable.

In this way a single model of the inhaler can be adjusted to be used with different liquid pharmaceutical formulations.

Spray characteristics for example spray volume, spray shape, spray average particle charge depend on the characteristics of the liquid pharmaceutical formulation to be atomized. So the adjustability of the counter electrode distance allows for one model to be produced and be used for different liquid pharmaceutical formulations allowing cheaper production.

According to a favourable embodiment, the inhaler further comprises a counter electrode actuator capable of moving the nozzle and the counter electrode with respect to each other.

In this way the setting of the counter electrode distance can be controlled without touching the nozzle. Touching the nozzle may influence its characteristics by damage or dirt depositing on its surface. For example a rack and pinion allows fast adjustment. An endless screw with worm may provide for enhanced precision of adjustability depending the pitch of the endless screw.

According to a favourable embodiment, the nozzle and the counter electrode are movable with respect to each other along a direction of the longitudinal axis of the portion of the nozzle extending into the lumen.

In this way the counter electrode distance is adjustable with a substantially linear response with respect to the electric field established between the nozzle outlet and the counter electrode, thus setting the electronic inhaler for use with a selected liquid pharmaceutical for delivery to a selected tissue of the respiratory system becomes easier. Three dimensional configuration of the nozzle and the counter electrode is less of a concern when adjusting along a single axis.

In this way the discharge electrode distance may be adjusted along a single axis with less concern regarding the three dimensional arrangement of the nozzle, the counter electrode and the discharge electrode making adjustment easier.

According to a favourable embodiment, the nozzle outlet coincides with a cone basis plane perpendicular to the longitudinal axis of the portion of the nozzle extending into the lumen and the side of said cone basis plane facing the nozzle also faces the counter electrode.

In this way the counter electrode is positioned such that in use the particles from the spray do not move towards and deposit on the counter electrode, such wetting and fouling of the counter electrode with pharmaceutical formulation may interfere with the electrical field and result in sub-optimal delivery of a pharmaceutical formulation comprised in the spray to the targeted tissue, hence a dosing less than intended is provided in prior art in which over time more wetting and fouling occurs compared to the inhaler according the invention.

According to a favourable embodiment, the counter electrode is annular and arranged perpendicular and centered on a longitudinal axis of the portion of the nozzle extending into the lumen.

In this way the inhaler may be able to generate a spray of which a greater fraction can be delivered to the target tissue rendering the inhaler more efficient.

According to a favourable embodiment, the nozzle and/or counter electrode and/or the counter electrode actuator are configured to alter the counter electrode distance in a discrete manner.

Due to the discrete (i.e. step-wise) adjustability, preset settings are provided on the inhaler, allowing for example a manufacturer, general practitioner, pharmacist or user to adjust the inhaler with ease and reduced error, providing during use for a spray that reliably delivers a pharmaceutical formulation at the intended tissue. Form shape locks at discrete positions of the nozzle or the counter electrode actuator or ratchet or beaded type shapes may provide for discrete adjustability. This also subtly locks the setting in a desired position.

According to a favourable embodiment, the inhaler further comprises a counter electrode securing means for securing the nozzle in a position relative to the counter electrode.

In this way a manufacturer, general practitioner, pharmacist, or user can secure the setting of the inhaler after it has been set in a desired position and thereby assure a reliable delivery of a pharmaceutical formulation. The preset inhaler is less prone to being inadvertently altered by for example accidental manipulation, vibrations or improper use by a user.

Finally, the present invention relates to use of a nozzle in a method for adjusting an inhaler for inhaling a liquid pharmaceutical formulation or in an inhaler for inhaling a liquid pharmaceutical formulation, wherein the method is according any of claims 1 to 7 and/or the inhaler is according any of claim 8 to 19, 20 or 21.

In this way inhalers can be adjusted to market demands and/or refurbished cheaply and easily for use with a selected liquid pharmaceutical formulation.

Figure 1B:
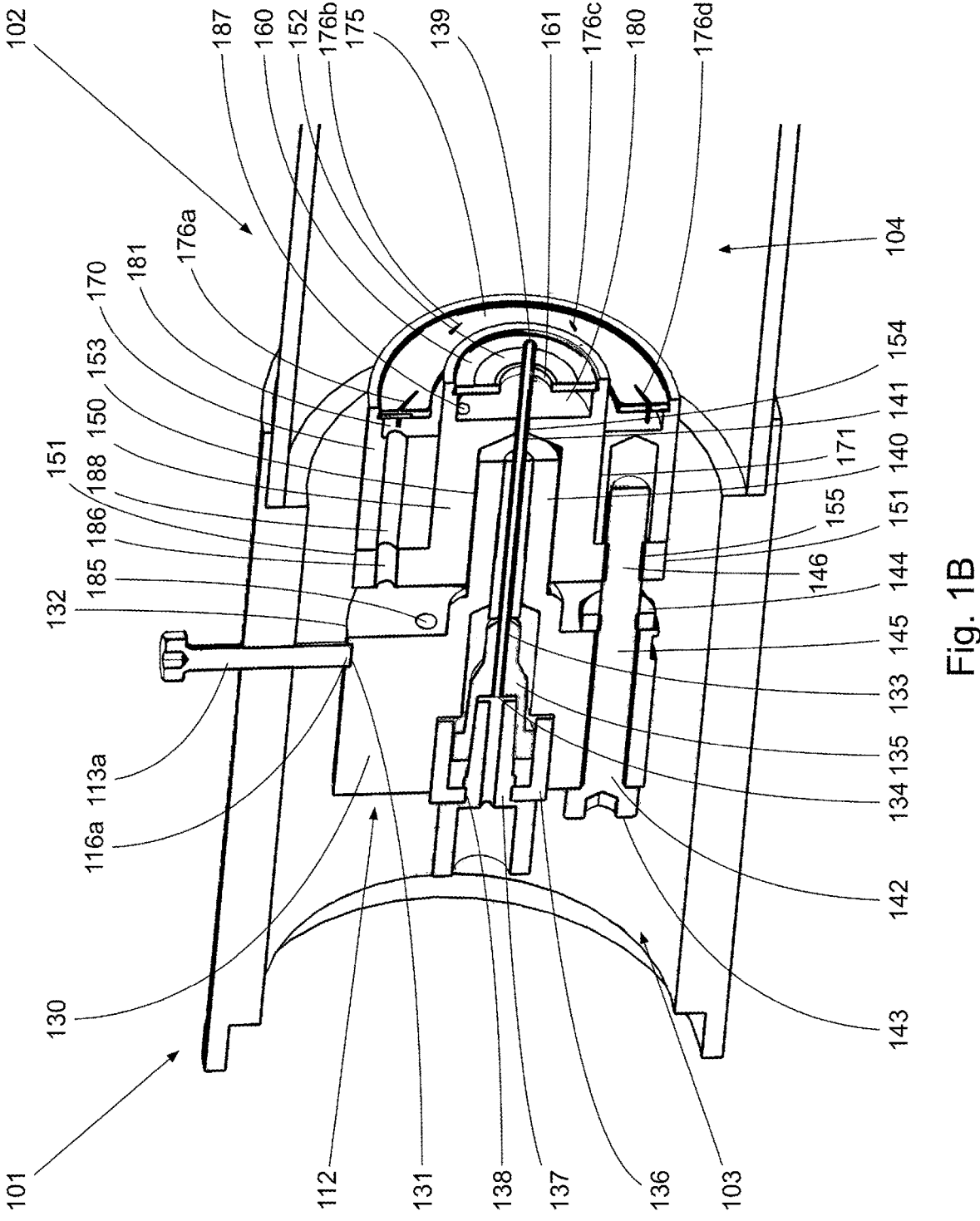
Figure 2:
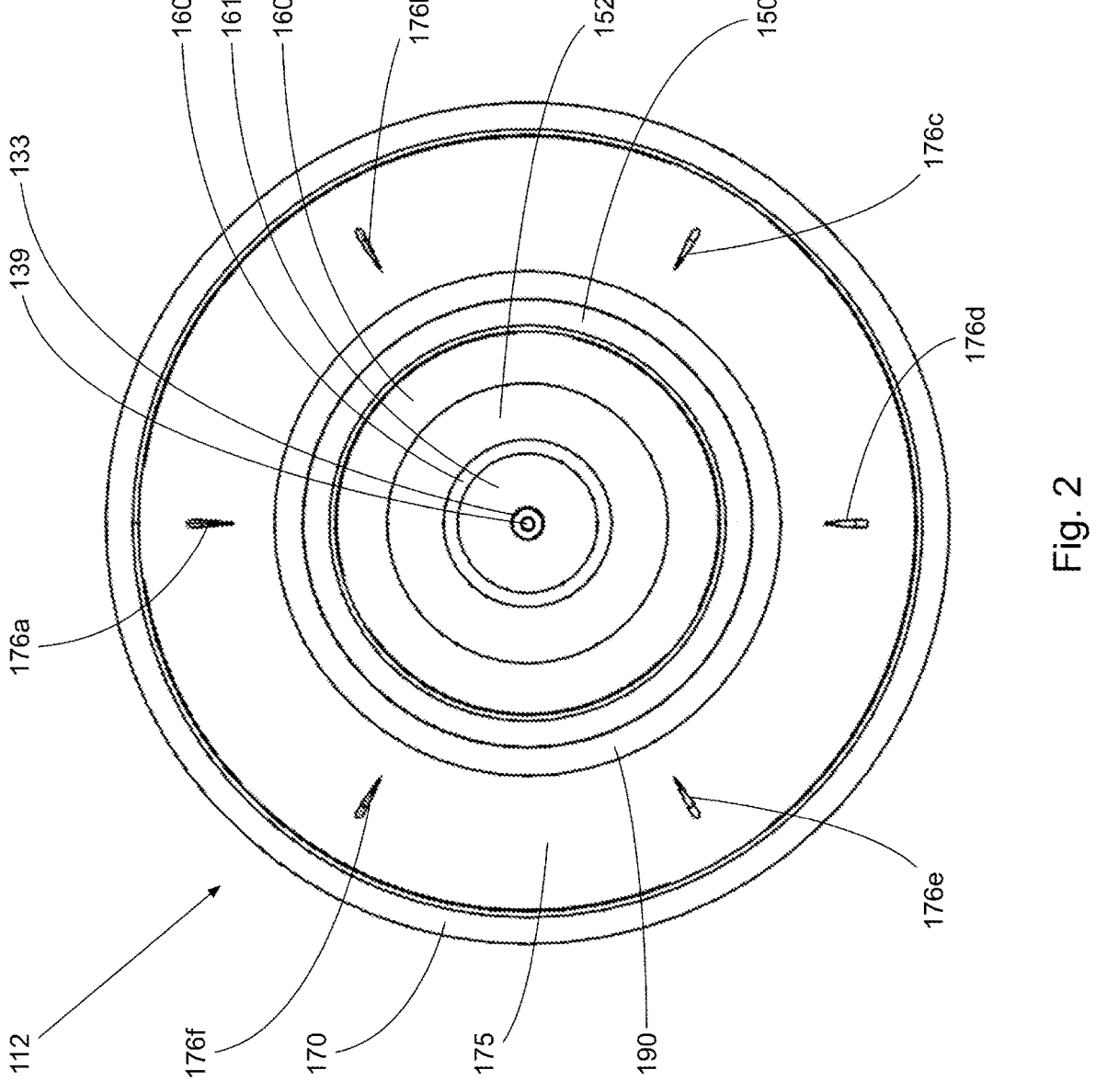

The present invention will now be illustrated with reference to the drawing where FIG. 1a shows a cut out view of an inhaler according the invention;

FIG. 1b shows a cross section along the longitudinal axis of the embodiment according FIG. 1a; and FIG. 2 shows a top view of the inhaler body of the embodiment according FIG. 1a.

An exemplary embodiment is an inhaler 100 with a tubular shape comprising two releasably coupled portions, a body portion 101 composed of a first cylindrical part 101a with a body portion circumferential wall and open ends and a mouth piece portion 102 composed of a second cylindrical part 102a also releasably coupled to a third cylindrical part 102b, both with circumferential walls and open ends as well. The body portion envelops a body portion lumen 103 and the mouth portion envelops a mouth portion lumen 104. The inhaler 100 has a longitudinal axis along its length running through center lines of the three cylindrical parts 101a, 102a and 102b. The lumina 103 and 104 form an air conduit through which air may flow from an air inlet opening 106 in an air inlet lid 105 covering the inhaler inlet 108 of the body portion 101 towards the inhaler outlet 110, allowing a user to inhale a flow of air. The air inlet lid 105 also comprises a slot 107 through which wiring for supplying electricity or a tube for supplying the liquid pharmaceutical formulation may pass allowing to take away the air inlet lid 105 or replace it with a different air inlet lid if operation of the inhaler requires more or less air to flow through the air conduit of the inhaler 100. Removal of the air inlet lid 105 also allows access to adjustment means of the inhaler 100 as explained later. A closed outlet lid 111 may be fitted for storage of the inhaler 100 and may be taken off before use. The inhaler outlet lid 111 prevents dirt from entering the air conduit through the inhaler outlet 110 into the lumen 105 of the mouth piece portion 102.

The body portion 101 holds an inhaler body 112. The inhaler body 112 is also cylindrical in shape. The center line of the inhaler body 112 is aligned along the longitudinal axis of the inhaler 100. The inhaler body 112 is fastened in the interior of the body portion 101 by three bolts, bolt 113a, bolt 113b and bolt 113c (not shown due cut out) engaged with their threads in matching threads in threaded through holes in the cylindrical wall 115 of the body portion 101. The bolt head 114a, bolt head 114b and bolt head 114c (not shown due cutout) are located at the outside of the body portion 101 allowing to tighten or release the bolts 113a, 113b and 113c. The bolts lengths are extending into the lumen 104 of the body portion 101. The bolts 113a, 113b and 113c are engaged with their respective distal tips 116a, 116b and 116c, the latter two blocked from view by the inhaler body 112, with a groove 131 present in the outer surface of a cylindrical wall 132 of the inhaler body 112 holding the inhaler body 112 centered in the air conduit inside the inhaler 100. In that way air may pass from the inhaler inlet 108 through the air conduit along the inhaler body 112 suspended in the center of the body portion lumen 103 and subsequently through the mouth portion lumen 104 to be inhaled via the inhaler outlet 110 by a user. When in operation the air flow may comprise the atomized pharmaceutical formulation. Further details on the inhaler body are discussed in FIG. 1b.

FIG. 1b shows a cross section along the longitudinal axis of the embodiment according FIG. 1a. The inhaler body 112 is formed by three parts cylindrical in shape, a nozzle part 130, a counter electrode part 150 and a discharge electrode part 170. The center lines of the individual inhaler body parts 130, 150 and 170 are aligned along the longitudinal axis as well. The nozzle part 130, the counter electrode part 150 and the discharge electrode part 170 are movable relative to each other along the longitudinal axis of the inhaler.

The nozzle part 130 is held in place by the distal tips 116a, 116b and 116c of the three respective bolts 113a, 113b and 113c engaged with the groove 131 provided in the outside surface of nozzle part cylindrical wall 132, suspending said nozzle part 130 in the center of the body portion 101. The nozzle part 130 comprises a capillary nozzle 133 with a nozzle inlet 134 associated with a female Luer-Lok fitting 135. The nozzle with the female Luer-Lok fitting 135 is removably seated in a through hole through the center line of the nozzle part. The female Luer-Lok fitting 135 and nozzle 133 are held in place by retaining element 136. The retaining element 136 has a through hole through which a male Luer-Lok fitting 137 is inserted into the female Luer-Lok fitting 135. A reservoir may be connected directly to or alternatively by means of a tube to the male Luer-Lok fitting 137. A through hole in the retaining element 136 acts as a snap lock on the male Luer-Lok fitting 136 by fitting into a groove 138 provided on said fitting. This allows a liquid pharmaceutical formulation to enter the nozzle 133 and pass through it. At the other end of the nozzle 133 opposing the nozzle inlet 134, a nozzle outlet 139 is provided from which a liquid pharmaceutical formulation may be atomized into a spray inhalable by a user. The nozzle 133 is partially surrounded by a rigid nozzle sleeve 140 protecting the fragile nozzle, a nozzle terminal section 141 of the nozzle 133 close to the nozzle outlet 139 is not covered by the nozzle sleeve 140.

The counter electrode part 150 with a cylindrical shape and provided with a flange 151 comprises a counter electrode 152 and a nozzle shaft 153. The nozzle shaft 153 holds the nozzle sleeve 140 and allows for slideable movement of the counter electrode part 150 with respect to the nozzle part 130 along the longitudinal axis. The nozzle shaft 153 presents a nozzle opening 154 at its end through which the terminal nozzle section 141 passes. The nozzle part 130 also comprises an endless screw 142 freely rotatable engaged with the nozzle part 130, a bolt head 143 and a nut 144 hold the endless screw worm shaft 145 in place, allowing rotation of the endless screw 142 and a worm 146. The endless screw 142 is engaged with a threaded through hole 155 in the flange 151 provided on the counter electrode part 150. Rotation of the endless screw 142 allows moving the counter electrode part 150 relative to the nozzle part 130 in either direction along the longitudinal axis. The nut 144 can also be tightened to prevent the endless screw 142 from rotating effectively locking the position and thus distance of the nozzle outlet 139 with respect to the counter electrode 152. The counter electrode part 150 also presents a base 160 with a base opening 161 and a surface facing the mouth piece lumen 104. At the surface of the base the annular counter electrode 152 is provided centered around the longitudinal axis along which axis the nozzle 133 extends through the base opening 161 into the mouth piece lumen 104 with its nozzle outlet 139 debouching into said lumen. The counter electrode 152, which is annular, has a width of 2 mm and is positioned with its inner diameter at a distance of 6 mm from the longitudinal axis. The nozzle outlet 139 extends 10 mm into the lumen of the second portion with respect to a base plane coinciding with the counter electrode 152 and the base 160 but is adjustable in a range of 5 mm from said base plane in a direction away from the lumen to 25 mm from said base plane in a direction towards lumen. The preferred range of adjustment is 0-20 mm from said base plane in a direction towards the lumen reducing wetting of the counter electrode 139.

The discharge electrode part 170 comprises a counter electrode shaft 171 for housing the counter electrode part 150 and is slidably arranged around the counter electrode part 150 by means of said shaft 171.

The discharge electrode part 170 can be moved with respect to the nozzle part 130 using a second endless screw with its worm shaft freely rotatable in a through hole in the nozzle part 130 and secured by a nut. The worm of said endless screw extends via a through hole allowing free rotation in the flange 151 of the counter electrode part 150. Said worm is engaged with a matching threaded hole in the discharge electrode part 170 allowing to move the discharge electrode part 170 relative to the nozzle part 130 (not shown). In this embodiment that allows for an adjustability of the discharge electrode along the longitudinal axis relative to the nozzle of 0 to 50 mm in the direction away from the nozzle outlet 139. It is foreseen that in another embodiment a discharge electrode part may be adjustable relative to a counter electrode part to the same effect.

The discharge electrode part 170 presents a discharge electrode 175 in the form of an annular ring centered on the longitudinal axis and is provided with a plurality of sharp protrusions 176, discharge portion 176a, discharge portion 176b, discharge portion 176c and discharge portion 176d from which charged particles may be emitted from their distal ends. The discharge portions 176a, 176b 176c and 176d, 6 in total of which 2 not shown, are directed towards the mouth piece lumen 104 with their distal ends, with respect to the counter electrode 175, pointing towards a volume near the nozzle outlet 139 where the spray is to be formed. The distal ends of the discharge portions 176a, 176b 176c and 176d are located at a distance of 13 mm from the longitudinal axis of the inhaler 100 and at a distance of 5 mm from the base plane coinciding with the counter electrode 152 and the base 160 at the side of the plane facing away from the mouth piece lumen 104 of the second portion. The distal ends comprised in the discharge electrode may be moved relative to the nozzle outlet 139 by actuating the second endless screw. The size of the discharge electrode part 170 along the direction of the longitudinal axis is relatively short compared to the size of the counter electrode part 150, this allows the discharge portions to be positioned at a range of distances relative to the nozzle outlet 139, at both sides of the base plane. When sparking occurs with a particular liquid pharmaceutical formulation the distance of discharge electrode 152 with respect to the nozzle outlet 139 may be increased to reduce sparking. When spray deposits on the inner surface of the mouth piece portion 102 decreasing said distance may allow for improved discharging of particles in the spray, and may thus result in more efficient delivery of the atomized pharmaceutical formulation to the target tissue of the user.

The counter electrode part 150 comprises a counter electrode circuitry cavity 180 and the discharge electrode part 170 comprises a discharge electrode circuitry cavity 181. The nozzle part 130 comprises an electricity conduit 185, the counter electrode part 150 comprises an electricity conduit 186 in its flange 151 and an electricity conduit 187 through its main body and the discharge electrode part 170 also comprises an electricity conduit 188. These cavities and conduits may house electrical components connecting the counter electrode 152 to ground and connecting the discharge electrode 175 to a power supply unit thereby reducing interference of said electronic components and wiring with the air flow in use through the body portion lumen 103 or the relative movement between the nozzle part 130, the counter electrode part 150 and the discharge electrode part 170 when adjusting. Establishing a potential on the nozzle outlet 139 is achieved by connecting the nozzle 133 to a power supply unit via wiring or the liquid pharmaceutical solution.

FIG. 2 shows a view of the inhaler body 112 from the lumen of the mouth piece portion 102. The nozzle outlet 139 is facing the viewer and centered on the longitudinal axis of the inhaler 100. The nozzle 133 is protruding through the base opening 161 in the base 160 of the counter electrode part 150, the base opening 161 allowing movement of the nozzle 133 through the base 160 and electrically isolating the two from each other. The base opening 161 is adjacent to the base 160 comprising the counter electrode 152 integrated in its surface. The base 160 is held by a form fit snap lock of the outer edge of the base 160 in a groove in the circumferential wall of the circuitry cavity 180 in the counter electrode part 150. The discharge electrode part 170 comprises the discharge electrode 175 with the 6 sharp protrusions 176 from which discharge portions 176a, 176b, 176c, 176d, 176e, 176f the discharging particles may emerge when in function. The 6 protrusions 176, including discharge portion 176e and discharge portion 176f not shown in FIG. 1a, are directed towards the longitudinal axis of the inhaler towards the volume in which the nozzle 133 may discharge the liquid pharmaceutical formulation as a spray during operation. The distal ends of the 6 discharge portions 176a-176f are located at equal distance from the nozzle outlet and are evenly spread around the nozzle outlet allowing a symmetrical discharge of a spray to be formed from the nozzle outlet 139. The discharge electrode 175 is also held by a form fit snap lock of its outer edge in a groove in the circumferential wall of the circuitry cavity 181 in the discharge electrode part 170. The discharge electrode 175 is located at a distance from the outer wall of the counter electrode part 150 creating a gap 190 electrically isolating the discharge electrode 175 from the counter electrode part 150.

The invention claimed is:

1. A method comprising:
providing an inhaler for inhaling a liquid pharmaceutical formulation, the inhaler including:
a mouth piece portion comprising a circumferential wall extending from the edges of an inhalation opening, said circumferential wall enveloping a lumen, and
a body portion coupled to the mouth piece portion, the body portion comprising a body with a base, said base facing the lumen and defining a limit of the lumen of the mouth piece portion, said body further comprising:
i) a nozzle comprising a nozzle inlet at a first end of the nozzle for receiving a liquid pharmaceutical formulation and a nozzle outlet at a second end of the nozzle for discharging said pharmaceutical formulation, wherein the nozzle passes through the base and a portion of the nozzle comprising the nozzle outlet extends into the lumen,
ii) a counter electrode, and
iii) a discharge electrode,
wherein the counter electrode is arranged at the base closer to the nozzle as compared to the discharge electrode at a counter electrode distance from the nozzle outlet, said counter electrode distance defining an electric field path, and
the discharge electrode comprising a discharge portion arranged farther from the nozzle as compared to the counter electrode, said discharge portion being at a discharge electrode distance from the nozzle outlet, wherein the discharge electrode distance is larger than the counter electrode distance;
the inhaler further including:
a power supply electrically connected to at least one of the nozzle, the counter electrode, and the discharge electrode, and
an air inlet for allowing air for inhaling to enter the lumen;
the method further comprising a step of adjusting the discharge electrode distance.

2. The method according to claim 1, wherein the inhaler further comprises a discharge electrode actuator capable of moving the nozzle and the discharge electrode with respect to each other; and
wherein in the method the step of adjusting the discharge electrode distance is performed by moving the nozzle and discharge electrode with respect to each other.

3. The method according to claim 1, wherein the inhaler further comprises a discharge electrode securing means for securing the nozzle in a position relative to the discharge electrode; and
the method further comprises a step of securing the nozzle in a position relative to the discharge electrode.

4. The method according to claim 1, further comprising a step of adjusting the counter electrode distance, wherein the step of adjusting the counter electrode distance is performed by truncating the portion of the nozzle extending into the lumen.

5. The method according to claim 1, wherein the inhaler further comprises a counter electrode actuator capable of moving the nozzle and the counter electrode with respect to each other; and
the method further comprising a step of adjusting the counter electrode distance, wherein the step of adjusting the counter electrode distance is performed by moving the nozzle and the counter electrode with respect to each other.

6. The method according to claim 1, wherein the inhaler further comprises a counter electrode securing means for securing the nozzle in a position relative to the counter electrode; and the method further comprises a step of securing the nozzle in a position relative to the counter electrode.

7. The method according to claim 1, wherein the nozzle of the inhaler is a removable nozzle; and the method further comprising a step of adjusting the counter electrode distance, wherein the step of adjusting the counter electrode distance is performed by replacing the removable nozzle with a replacement nozzle, said replacement nozzle being shorter or longer with respect to the removable nozzle or being of a same size as the removable nozzle.

8. The method according to claim 1, wherein the nozzle comprises a marking; and during the step of adjusting the counter electrode distance the marking is used for guiding said adjusting.

9. An inhaler for inhaling a liquid pharmaceutical formulation, said inhaler comprising:

a mouth piece portion comprising a circumferential wall extending from the edges of an inhalation opening, said circumferential wall enveloping a lumen, and a body portion coupled to the mouth piece portion, the body portion comprising a body with a base, said base facing the lumen and defining a limit of the lumen of the mouth piece portion, said body further comprising:

i) a nozzle comprising a nozzle inlet at a first end of the nozzle for receiving a liquid pharmaceutical formulation and a nozzle outlet at a second end of the nozzle for discharging said pharmaceutical formulation, wherein the nozzle passes through the base and a portion of the nozzle comprising the nozzle outlet extends into the lumen, ii) a counter electrode, and iii) a discharge electrode, wherein the counter electrode is arranged at the base closer to the nozzle as compared to the discharge electrode at a counter electrode distance from the nozzle outlet, said counter electrode distance defining an electric field path, and the discharge electrode comprising a discharge portion arranged farther from the nozzle as compared to the counter electrode, said discharge portion being at a discharge electrode distance from the nozzle outlet, wherein the discharge electrode distance is larger than the counter electrode distance;

the inhaler further comprising:

a power supply electrically connected to at least one of the nozzle, the counter electrode, and the discharge electrode, and an air inlet for allowing air for inhaling to enter the lumen; characterized in that the discharge electrode distance is adjustable.

10. The inhaler according to claim 9, wherein the discharge electrode comprises a plurality of discharge portions, said discharge portions at equal discharge electrode distance from the nozzle outlet and evenly spread around the longitudinal axis of the portion of the nozzle extending into the lumen.

11. The inhaler according to claim 9, wherein the nozzle and the discharge electrode are movable with respect to each other along a direction of the longitudinal axis of the portion of the nozzle extending into the lumen.

12. The inhaler according to claim 9, wherein the discharge portion is located outside the lumen.

13. The inhaler according to claim 9, wherein a distal end of the discharge portion is directed to the longitudinal axis of the portion of the nozzle extending into the lumen.

14. The inhaler according to claim 9, wherein the nozzle comprises a marking.

15. The inhaler according to claim 9, wherein the counter electrode distance is adjustable.

16. The inhaler according to claim 9, wherein the inhaler further comprises a counter electrode actuator capable of moving the nozzle and the counter electrode with respect to each other.

17. The inhaler according to claim 9, wherein the nozzle and the counter electrode are movable with respect to each other along a direction of the longitudinal axis of the portion of the nozzle extending into the lumen.

18. The inhaler according to claim 9, wherein the nozzle outlet coincides with a cone basis plane perpendicular to the longitudinal axis of the portion of the nozzle extending into the lumen and the side of said cone basis plane facing the nozzle also faces the counter electrode.

19. The inhaler according to claim 9, wherein the counter electrode is annular and arranged perpendicular and centered on a longitudinal axis of the portion of the nozzle extending into the lumen.

20. The inhaler according to claim 9, wherein the nozzle and/or counter electrode and/or the counter electrode actuator are configured to alter the counter electrode distance in a discrete manner.

21. The inhaler according to claim 9, wherein the inhaler further comprises a counter electrode securing means for securing the nozzle in a position relative to the counter electrode.

* * * * *